(12) United States Patent
Shoenfeld

(10) Patent No.: US 8,770,479 B1
(45) Date of Patent: Jul. 8, 2014

(54) MEDICAL STORAGE CABINET WITH RFID INVENTORY

(71) Applicant: Norman A. Shoenfeld, Cypress, TX (US)

(72) Inventor: Norman A. Shoenfeld, Cypress, TX (US)

(73) Assignee: S&S X-ray Products, Inc., Pen Argyl, PA (US)

( * ) Notice: Subject to any disclaimer, the term of this patent is extended or adjusted under 35 U.S.C. 154(b) by 2 days.

(21) Appl. No.: 13/739,329

(22) Filed: Jan. 11, 2013

(51) Int. Cl.
*G06K 19/00* (2006.01)

(52) U.S. Cl.
USPC ............ 235/385; 235/375; 235/487; 235/492

(58) Field of Classification Search
USPC .............................. 235/487, 492; 340/10, 572
See application file for complete search history.

(56) References Cited

U.S. PATENT DOCUMENTS

| 6,861,993 | B2 | 3/2005 | Waldner |
| 7,348,884 | B2 | 3/2008 | Higham |
| 7,648,065 | B2 | 1/2010 | Marino |
| 7,990,272 | B2 | 8/2011 | Wass et al. |
| 7,994,897 | B2 | 8/2011 | Azevedo et al. |
| 8,174,392 | B1 | 5/2012 | Saghbini et al. |
| 2009/0058744 | A1 | 3/2009 | Marino |
| 2009/0267772 | A1* | 10/2009 | Dehnadi ............... 340/572.8 |
| 2010/0141386 | A1* | 6/2010 | Kim et al. ............... 340/10.1 |
| 2010/0141457 | A1* | 6/2010 | Wass et al. ............. 340/572.8 |

* cited by examiner

*Primary Examiner* — Matthew Mikels
(74) *Attorney, Agent, or Firm* — Bernhard P Molldrem, Jr.

(57) ABSTRACT

A medication and/or medical supplies storage cabinet of all-steel construction has an RFID transducer or reader with an antenna array (i.e., an antenna or series of antennas) carried on a vertical elevator at the rear of the cabinet's metal shelves and drawers. The metal shelves, sides and back of the cabinet define successive compartments in which RFID-tagged item are stored. The vertical elevator may have a drive motor, e.g., gear-motor controlled by a computer associated with the cabinet. There may be a wall or window of a suitable radiolucent material at the rear of the cabinet to permit the RFID energy to radiate between the RFID antenna array and any RFID-tagged inventory items contained in the respective compartments or drawers.

9 Claims, 4 Drawing Sheets

MEDICAL STORAGE CABINET WITH RFID INVENTORY

BACKGROUND OF THE INVENTION

This invention relates to cabinets for storing and dispensing prescription medical items and medical and hospital supplies, which can be free standing, mounted on rollers, or built into a wall, for providing practitioners with access to the medications and other items. The invention is also concerned with a cabinet made of steel or other electrically conductive material, which may be radiopaque, and provided with a built-in RFID (Radio Frequency Identification) transducer for interrogating RFID-tagged inventory items within the cabinet, and reading the RFID responses from such items.

Many medical supply items, e.g., syringes, bandages and dressings, disinfectants, catheters, and patient medications, need to be available to health practitioners in the places where the patient is located. At the same time, it is important for the hospital supply technicians and pharmacy technicians to be aware of the inventory levels of items in the supply cabinets throughout the facility, so that they will be properly stocked, and when the items are needed they can be given without delay to the patient. In some cases, the identification of items within the cabinet, and the number of each such item can be discerned automatically, e.g., by reading RFID tags that are attached to the items or incorporated into the packaging of the item.

In most cases, steel cabinets are preferred because of their durability and reasonable price. However, where the cabinets and the shelves and compartments are formed of steel, the low-level RF signals used to interrogate the RFID tags do not penetrate into the compartments between shelves; and the low-level RF signals returned from RFID tags on the items in the cabinets do not pass out through the metal walls and shelves. When the cabinets are made of a non-metal, i.e., plastic or synthetic material, the RF signals can reach between the RF transducer or reader and the inventory items, but it is not possible to know what items are stored in which compartments. Moreover, in cabinet arrangements in which the RFID reader or transducer is located in a fixed location in or on a cabinet, the reflections of signals within the cabinet creates dead zones that make it difficult to capture returns from each and every one of the inventory items.

These cabinets may have electronic locking and unlocking features, to limit access only to authorized medical personnel, and incorporate software features giving them the capability of maintaining an audit trail of access.

OBJECTS AND SUMMARY OF THE INVENTION

Accordingly, it is an object of the present invention to provide medical supply cabinet that is conveniently made of steel, with steel shelves creating individual compartments within the cabinet, and with a feature employing an RFID transducer for recording inventory of items in the cabinet, but which avoids the drawbacks of the prior art, and improves upon inventory count accuracy.

It is another object to provide a medical supply cabinet or cart that moves the incorporated RFID antenna array to each respective space or compartment within the cabinet to conduct a count or inventory of the inventory items contained within the respective compartment. The cabinet may also incorporate one or more pull-out drawers, and in that case the RFID transducer/antennas are adapted to read the RFID tags of items within each respective drawer. Of course, as used in this description and claims, the terms "shelf", "compartment" and "drawer" should be read broadly to cover any equivalent compartment in which inventory items may be contained or stored.

In accordance with an aspect of the present invention, a steel storage cabinet is formed having a frame, side walls, a top, a base, a back, and several horizontal shelves arranged one above another in said cabinet. These shelves define between them respective storage compartments. For each compartment there may be an access door at the front of the cabinet. The RFID-tagged items may be stored in an orderly fashion in the various compartments. In this case, the side walls, top, base, back, shelves and doors are formed of steel. As mentioned earlier, the steel or metal can interfere with reading RFID tags, and is relatively opaque to the RF waves used in RFID techniques. In addition, the configuration of the shelves and metal cabinet doors, sides, and back acts as a Faraday cage and makes the contained tags difficult to interrogate.

An RFID inventory interrogation and data collection arrangement within cabinet, incorporates one or more RFID transducer or reader, with attached antenna(s) or antenna array(s) that are capable of emitting an RFID interrogate signal and are also capable of receiving from the RFID-tagged items RFID response signals. A vertical elevator is disposed within the cabinet to the rear of the shelves, and the RFID antenna array is mounted on this elevator so it can be positioned properly to take inventory of each given compartment, one at a time. A drive arrangement controllably drives the elevator up and down to position the RFID antenna array so that it is properly aligned with a selected one of the compartments. A computer control or similar equipment associated with the cabinet controls the RFID transducer to cause same to interrogate the RFID-tagged items within the selected compartment and then to interpret the RFID responses received from the RFID-tagged items. This may be implemented as a suitably programmed computer connected by a wire or wireless connection to the RFID transceiver and to the drive arrangement. In practice, the RFID reader or transducer is fixedly mounted in the cabinet, and is connected by cables to the antenna array, which may be one or several antennas mounted on the vertical elevator or slide.

When the cabinet includes drawers, each of the drawers may have a rear wall at its distal end (i.e., the end facing or positioned adjacent the back wall of the cabinet when the drawer is pushed closed) that is at least partly formed of a radiolucent material (e.g., a sturdy plastic resin such as Lexan or Plexiglas) that permits the RFID interrogate and response signals to penetrate.

The vertical elevator can be implemented, e.g., as a vertical slide at the back of the cabinet, or as an indexed belt oriented vertically at the rear of the cabinet, or as a vertical screw drive. In each case, the RFID reader/transducer is affixed within the cabinet and the antenna array is mounted on the slide, or belt, or screw drive so it can be moved up and down through its various positions. The drive arrangement can be implemented as a drive motor which may for example be a servomotor, a DC gearmotor, an AC gearmotor, or a stepper motor. The antenna array may be one or more antennas, e.g., circuit boards, mounted side to side to match the width of the cabinet shelves. Alternatively, the reader/transducer could also be mounted on the vertical slide or belt, but this is not currently preferred.

The back of the cabinet may incorporate a long vertical window, e.g. a sheet of Lexan, or a number of individual windows for each respective compartment, with the window being formed of a radiolucent material that permits the RFID interrogate signals and RFID response signals to penetrate. In order to avoid the problem of dead spots or dead zones, the drive arrangement can move the RFID antenna array through a number of positions at each selected one of the compartments. This may be done at discrete steps, or the arrangement may sweep the RFID antenna array through several positions.

The associated computer can be programmed to conduct an inventory each time that the cabinet is accessed, to ascertain what items have been removed, and thus create an access inventory history or audit trail.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 3:
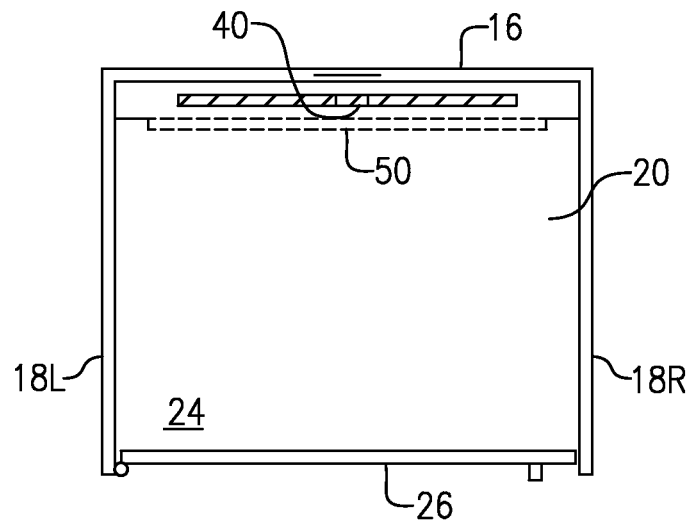
FIG. 3 is downward sectional view taken at cut line 3-3 of FIG. 1.
Figure 4:
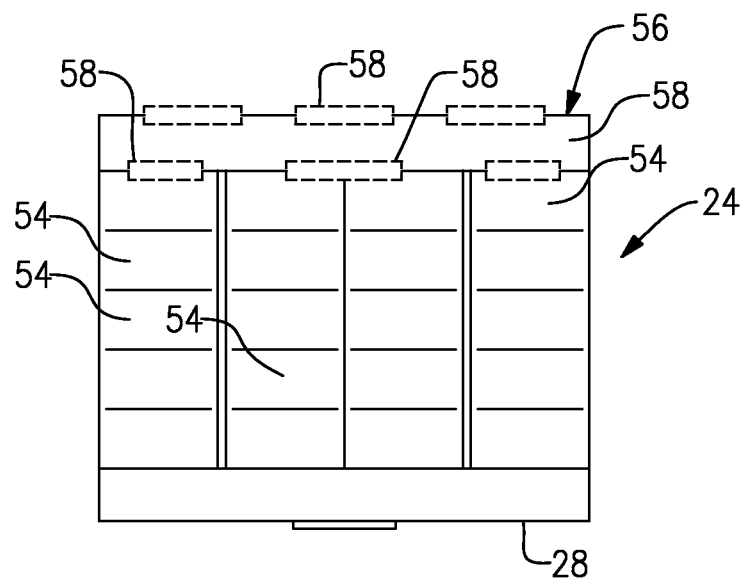
FIG. 4 is a downward sectional view of a drawer taken at cut line 4-4 of FIG. 1.
Figure 5:
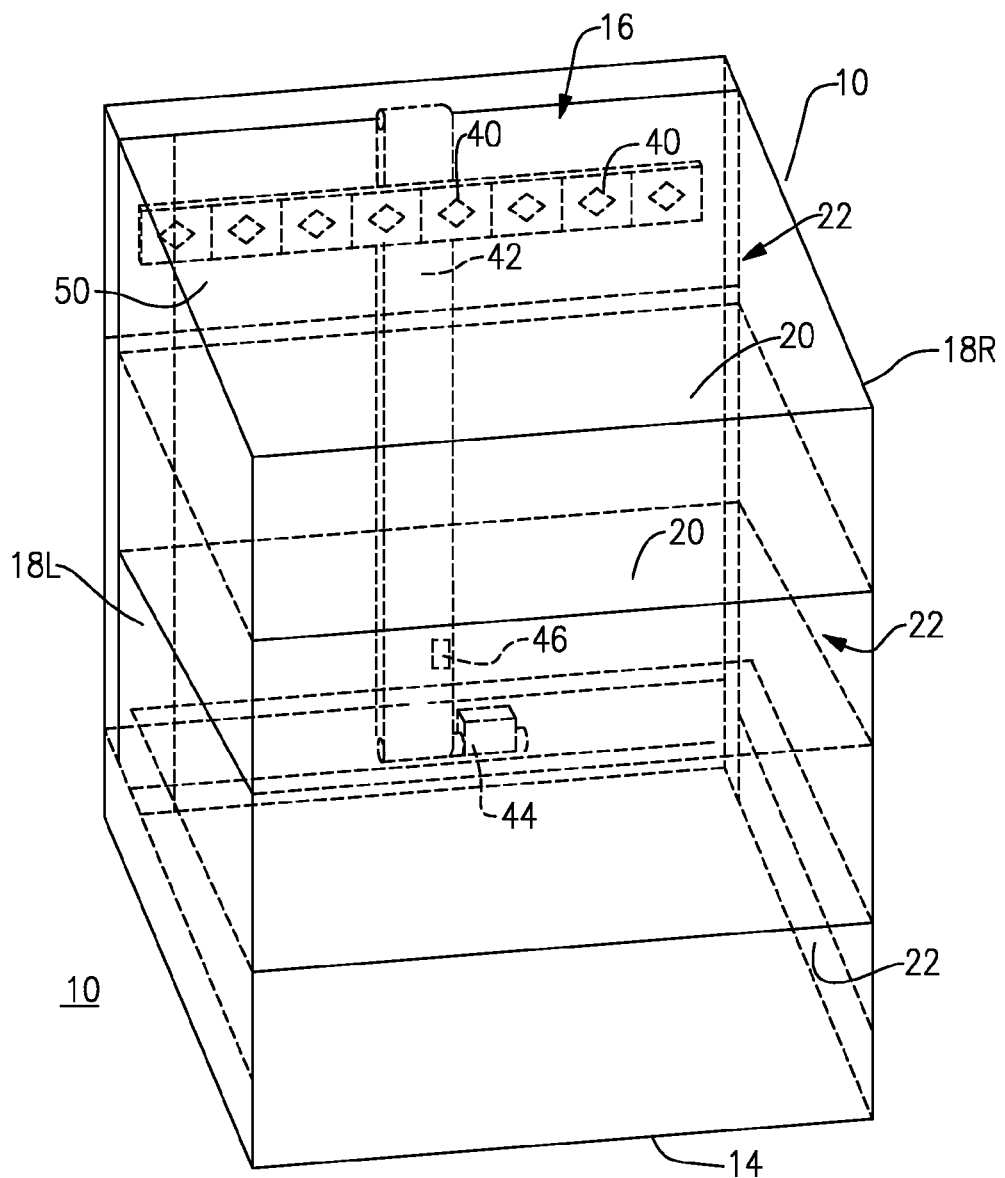
FIG. 5 is a schematic view of this embodiment.

With reference to the Drawing, FIGS. 1 to 4 illustrate a steel medications cabinet or medical supply cabinet 10, formed of a top 12, base 14, back 16, left and right side walls 18L and 18R, and a number of internal shelves 20 (see cross section (FIG. 2) and also FIG. 5). These components are all of steel construction, and a steel frame of the cabinet holds all the components in place. The cabinet 10 may be a floor-standing model, or may be in the form of a cart 10 with wheels, rollers or casters, so as to be able to be rolled easily into a room or nursing station. The shelves 20 together with sides 18L, 18R, and top 12 define respective internal compartments 22, and there may be a number of pull-out drawers 24 as well; in this illustrative embodiment there is a stack of four drawers 24. The compartments 22 each have a door 26 hinged at one side, and a pull handle, and may have an electrically controlled latch that can be remotely or locally unlocked for access to the respective compartment. The drawers 24 each have a front panel 28 which may include a lock or latch.

At one side of the cabinet 10 there is a computer shelf 30 supporting a computer or PC 32, including a monitor 34, mouse 36 and keyboard. 38. An authorized user may employ the computer 32 to unlock and access a given one of the compartments or drawers to obtain the inventory items(s) contained therein.

Figure 1:
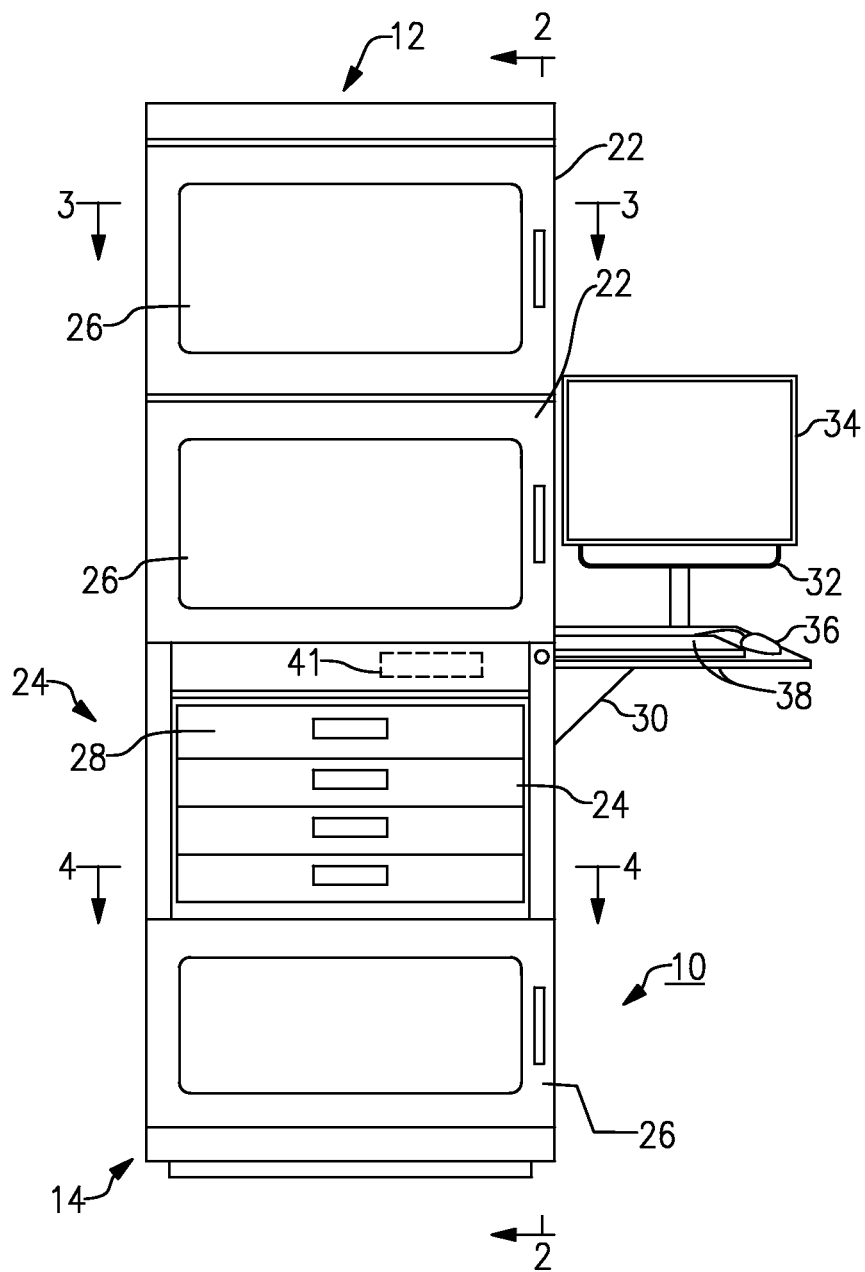
FIG. 1 is a front elevational view of a medical supply cabinet of steel construction that constitutes one possible embodiment of the present invention.
Figure 2:
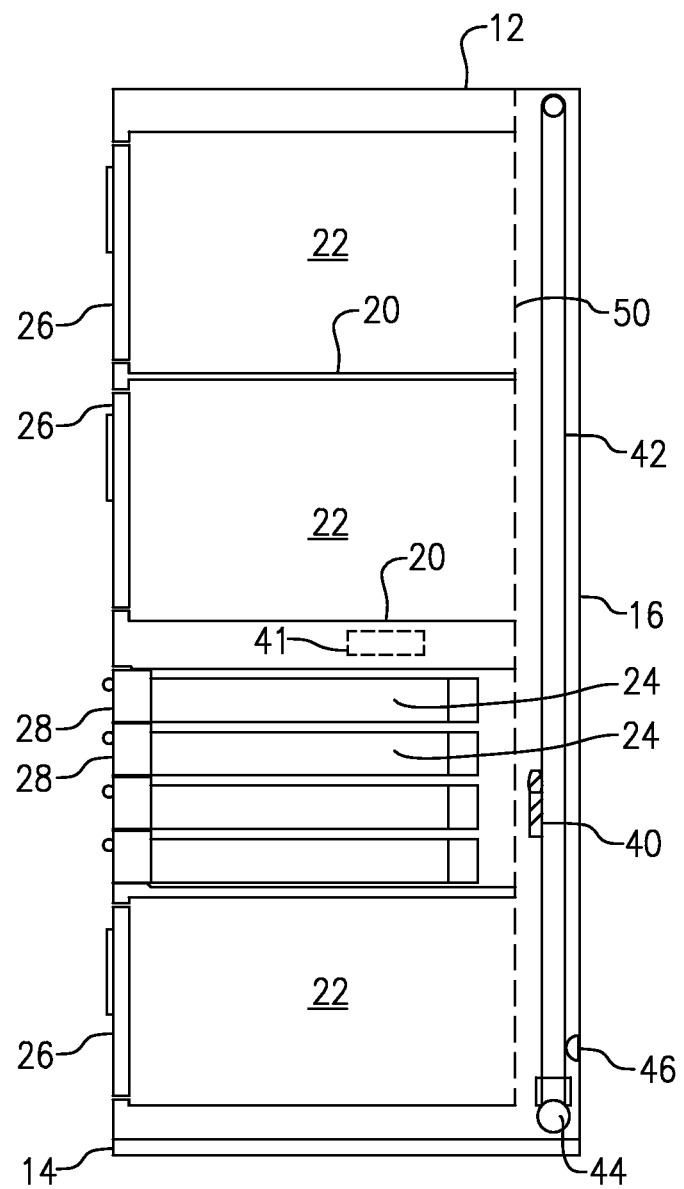
FIG. 2 is a sectional side elevation view, taken at the cut line 2-2 in FIG. 1.

As shown better in FIGS. 2, 3, and 5, an RFID antenna array 40 is disposed at the rear of the cabinet and is mounted on a vertical transport or elevator 42. The associated RFID transceiver 41 is mounted at a fixed location within the cabinet, and is connected by cables to the antenna array 40. The transceiver also has connections to receive power and network connection. In this illustrative embodiment the elevator 42 is an indexed belt drive, but in other possible embodiments the elevator may take the form of a screw drive or a slide mechanism adapted to raise and lower the RFID antenna array 40 along the height of the cabinet so that it traverses each of the compartments 22, and also traverses the vertical spaces occupied by the respective drawers 24. At the base 14 of the cabinet is a drive motor 44 for the vertical elevator 42, which may be an AC gearmotor, a DC gearmotor, a stepper motor, or a servo motor. An index reader or counter 46, which may consist of a potentiometer or an encoder, is positioned adjacent the belt of the elevator 42 to provide position information to the computer 32. The array 40 is formed of a series of antennas, each in the form of a rectangular circuit board, with the array occupying the width of the interior of the cabinet.

Each of the shelves 20 in the compartments 22 and each of the drawers 24 contains hospital supply or medical items and materials that will be needed or may be needed by an attending care giver in the course of hospital care. As a practical matter, each of the inventory items has a respective RFID tag, encoded with identifying data corresponding to the associated inventory item.

The power cord for connecting with the hospital AC power is not shown here.

A rear portion of the cabinet 10, disposed vertically behind the shelves 20 and drawers 24, is at least partly constructed of a radiolucent material 50, e.g., a plastic resin. This material allows the RFID signals to pass through without undue attenuation or scattering. This may be, as shown here, a long sheet of plastic material aligned with the vertical path of the RFID antenna array, or may be comprised of a number of discrete window elements arranged vertically so that the RFID antenna array 40 can be situated at more than one elevated position for each of the compartments. The radiolucent sheet 50 also serves to keep the cabinet contents isolated from the moving antenna array.

In this embodiment each drawer 24, as shown in FIG. 4, has several rows of compartments or bins 54, and can be of the same general configuration of the medications drawer disclosed in my earlier-filed U.S. patent application Ser. No. 13/291,462, filed Nov. 8, 2011, the contents of which are incorporated by reference herein.

The compartments 54 may, in some embodiments, have locking lids to limit access to the contents.

As shown here, the back or distal wall 56 of the drawer has a portion (or portions) 58 formed of a radiolucent material to allow the RFID energy to pass between the RFID antenna array 40 and the interiors of the compartments 54 in the drawer. These portions 58 may be windows formed in the back wall 56, where the latter is of steel construction, or may be a single vertical strip or sheet, or may constitute the entire construction of the back wall. Depending on the construction of the drawers, the radiolucent portion 58 may not be necessary, as a sufficient amount of the RF energy may pass between the antennas of the transducer or reader and the interior of the drawer.

The computer 32 is suitably programmed to control the drive motor 44 so as to position the RFID antenna array 40 at the vertical position(s) required to interrogate the contents of each of the spaces, i.e., the contents of each of the compartments 24 and drawers 22 in turn. The vertical elevator 42 can carry out small movements up and down at the rear of each space, so that the transducer 40 can scan around any dead zones or RF dead spots, and ensure a capture of all RFID tags in the respective space.

The computer 32 stores inventory information of all the RFID-tagged inventory items contained in the cabinet 10. The computer may also be suitably programmed to keep an inventory audit trail or accounting, based on successive scans, of which inventory items have been removed, and when, and which have been added to the inventory.

This arrangement enables the system to have database control over the exact locations of the medications and supplies. RFID coding of the medications or other contents of the cabinet permits the access to those materials to be recorded and tracked. Access controls associated with the cabinet computer 32 can also identify the person accessing the items, and the time of access. Similarly, methods employing RFID identification of individual medications can also be used for security and prevention of medication dispensing errors.

The individual cabinets configured for RFID inventory, as described here, may also be joined together using a daisy-chain i2C communications protocol, for tracking inventory of an array of cabinets.

The RFID reader backs of the cabinets can be made as a bolt-on option to be attached onto a standard (non-RFID) cabinet. This allows the cabinets to be constructed the same both with and without the RFID inventory feature, with the cabinet back, radiolucent window, RFID reader, RFID antenna array, and vertical elevator all constructed as a unit and bolted in place onto the cabinet when an RFID-capable cabinet is ordered, or if it is desired to convert a standard steel cabinet to a cabinet with the RFID automated inventory feature.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

What is claimed is:

1. Medical storage cabinet comprising a frame, side walls, a top, a base, a back, a plurality of horizontal shelves arranged one above another in said cabinet wherein successive ones of said shelves define between them respective storage compartments in which may be stored a plurality of RFID-tagged items; and for each compartment an access door disposed at a front side of the cabinet; wherein the side walls, top, base, back, shelves and doors are formed of steel;

an RFID inventory interrogation and data collection arrangement within said cabinet, including an RFID transducer having an antenna array capable of emitting an RFID interrogate signal and capable of receiving from said RFID tagged items RFID response signals, a vertical elevator disposed within said cabinet at a rear of said shelves, and on which said RFID antenna array is mounted, and a drive arrangement for controllably driving said elevator up and down to move said RFID antenna array to a position aligned with a selected one of said compartments; and means controlling the RFID transducer to cause same to interrogate the RFID-tagged items within the selected compartment and to interpret the RFID response signals received from said RFID-tagged items.

2. The medical storage cabinet according to claim 1 wherein said means controlling the RFID transducer includes a suitably programmed computer connected by a wire or wireless connection to said RFID transceiver and to said drive arrangement.

3. The medical storage cabinet according to claim 1 wherein said at least one of said compartments includes a plurality of locking drawers formed of steel.

4. The medical storage cabinet according to claim 3 wherein each of said drawers has a rear wall at a distal end that is positioned adjacent the back wall of the cabinet when the drawer is pushed closed, and said distal wall is at least partly formed of a radiolucent material that permits the RFID interrogate and response signals to penetrate therethrough.

5. The medical storage cabinet according to claim 1 wherein said vertical elevator includes a vertical slide oriented vertically at the back of said cabinet, with said RFID antenna array being mounted on said slide, and wherein said drive arrangement includes a drive motor selected from a group consisting of a servomotor, a DC gearmotor, an AC gearmotor, and a stepper motor.

6. The medical storage cabinet according to claim 1 wherein said vertical elevator includes an indexed belt oriented vertically at the back wall of said cabinet, with said RFID antenna array being mounted on said belt, and wherein said drive arrangement includes a drive motor selected from a group consisting of a servomotor, a DC gearmotor, an AC gearmotor, and a stepper motor.

7. The medical storage cabinet according to claim 1 wherein the back of said cabinet includes for each said compartment a window formed of a radiolucent material permitting the RFID interrogate and response signals to penetrate therethrough.

8. The medical storage cabinet according to claim 1 wherein said drive arrangement is adapted to position said RFID transceiver at a plurality of positions at each selected one of said compartments.

9. The medical storage cabinet according to claim 1 wherein said antenna array comprises a plurality of antenna boards disposed side to side to occupy substantially the width of the shelf of the associated compartment.

* * * * *